United States Patent [19]
Adams et al.

[11] Patent Number: 5,965,377
[45] Date of Patent: Oct. 12, 1999

[54] METHOD FOR DETERMINING THE PRESENCE OF MUTATED BRCA PROTEIN

[75] Inventors: Lorrie A. Adams, Westfield; Timothy J. Byrne, Springfield; Gabriel M. Cohn, East Longmeadow; Margaret T. Reece, Springfield, all of Mass.

[73] Assignee: Baystate Medical Center, Springfield, Mass.

[21] Appl. No.: 09/044,817

[22] Filed: Mar. 20, 1998

Related U.S. Application Data

[60] Provisional application No. 60/042,337, Mar. 24, 1997.
[51] Int. Cl.$^6$ .................. G01N 33/574; G01N 33/567; G01N 33/53
[52] U.S. Cl. ..................... 435/7.23; 435/7.1; 435/7.2
[58] Field of Search ................... 435/7.1, 7.21, 435/7.23

[56] References Cited

U.S. PATENT DOCUMENTS

| | | |
|---|---|---|
| 5,252,458 | 10/1993 | Liav et al. . |
| 5,283,190 | 2/1994 | Traish et al. . |
| 5,683,885 | 11/1997 | Kieback . |

FOREIGN PATENT DOCUMENTS

| | | |
|---|---|---|
| 0705903A1 | 8/1995 | European Pat. Off. . |
| WO9605308 | 8/1995 | WIPO . |
| WO9633271 | 4/1996 | WIPO . |
| WO 9633271 | 10/1996 | WIPO . |
| WO9808394 | 8/1997 | WIPO . |

OTHER PUBLICATIONS

Lianes et al. J. of National Cancer Institute. 86 (17), 1325–30, Sep. 1994.

Palfreyman et al. J. Immuno. Meth. 75, 383–395, 1984.

Gilliam, L.K. et al., "Production of a monoclonal antibody reactive with BRCA2 protein sequences", Eighty–Eight Annual Meeting of the American Association for Cancer Research, San Diego, CA, USA, Apr. 12–16, 1997. Proceedings of the American Association for Cancer Research Annual Meeting, vol. 38, Mar. 1997, at 243, XP002073283 (abstract).

Yoshio Miki et al., A Strong Candidate for the Breast . . . , Science, vol. 266, Oct. 7, 1994, at 66–71.

Richard Wooster et al., Identification of the Breast Cancer Susceptibility Gene BRCA–1, Nature, vol. 378, Dec. 21/28, 1995, at 789–792.

Ralph Scully et al., Location of BRCA–1 in Human Breast Cells and Ovarian Cells, Science, vol. 272, Apr. 5, 1996, at 123–124.

Donna Shattuck–Eidens et al., A Collaborative Survey of 80 Mutations . . . , J. Am. Med. Ass'n, vol. 273, No. 7, Feb. 15, 1995, at 535–541.

Chun–Fang Xu & Ellen Solomon, Mutations of the BRCA–1 Gene in Human Cancer, seminars in Cancer Biology, vol. 7, Feb. 1996, at 33–40.

S.V. Tavtigian et al., The Complete BRCA–2 Gene and Mutations . . . , Nature Genetics, vol. 12, Mar. 1996, at 333–337.

Simon A. Gayther et al., Variation of Risks of Breast and Ovarian Cancer . . . , Nature Genetics, vol. 15, Jan. 1997, at 103–105, and.

Cindy A. Wilson et al., Differential Subcellular Localization Expression and Biological Toxicity . . . , Oncogene, vol. 14, Jan. 1997, at 1–16.

*Primary Examiner*—Paula K. Hutzell
*Assistant Examiner*—Lin Sun-Hoffman
*Attorney, Agent, or Firm*—Mary R. Bonzagni Esq.; Holland & Bonzagni, P.C.

[57] ABSTRACT

This invention relates to a simple and reliable screening method for determining an individual's susceptibility to breast, ovarian, colon or prostrate cancer. This invention also relates to a test kit for use in conjunction with this method. The inventive method targets a specific alteration of the BRCA protein and identifies a non-invasive source of normal cells that express this protein.

22 Claims, No Drawings

METHOD FOR DETERMINING THE PRESENCE OF MUTATED BRCA PROTEIN this application is based in part on Provisional patent application Ser. No. 60/042,337, filed Mar. 24, 1997.

FIELD OF THE INVENTION

The present invention relates generally to a method for determining an individual's susceptibility to breast, ovarian, colon or prostate cancer.

BACKGROUND OF THE INVENTION

BRCA-1 and BRCA-2 gene mutations have been identified as being responsible for about 90% of all early-onset hereditary breast and ovarian cancers.

BRCA-1 and BRCA-2 gene mutations have also been associated with an increased risk of, or susceptibility to, colon or prostate cancer.

The full sequence of the BRCA-1 and BRCA-2 genes were discovered and/or published in October 1994 and December 1995, respectively. The availability of these sequences and the deduced amino acid sequences has allowed the generation of representative peptide sequences. These peptide sequences have been used as immunogens to raise antibodies capable of detecting specific regions of the BRCA-1 and BRCA-2 proteins.

Approximately 88% of BRCA-1 mutations have been reported to result in the production of a foreshortened protein, from which the terminal end sequences (i.e., carboxy-terminus (C-terminus)) of the BRCA-1 protein are missing. (See Donna Shattuck-Eidens et al., *A Collaborative Survey of 80 Mutations* . . . , J. Am. Med. Ass'n, Vol. 273 No. 7, Feb. 15, 1995, at 535–541). Data documenting the extent of BRCA-2 mutations, which also result in protein truncation, is available. (See Simon A. Gayther et al., Variation of risks of breast and Ovarian Cancer . . . , BRCA-2 gene, Nature Genetics, Vol. 15, 1997, January 1997, at 103–105). BRCA-1 mutations, however, are reported to have taken the form of single base alterations, single base deletions or multiple base deletions that result in frame shifts that end with downstream stop codons, producing truncation of the BRCA-1 protein consequent to the presence of a gene mutation. As is well known to those skilled in the art, a normal individual carries two unmutated alleles of the BRCA-1 protein while a susceptible individual inherits a normal allele from one parent and a mutated allele from the other parent. These normal and heterozygous allele pairs are carried in every nucleated cell within the body. In tumor tissue, the normal allele has frequently become altered, leaving the susceptible individual with no normal gene copies to produce normal, full-length BRCA-1 protein. In view of the above, it has been hypothesized by the present inventors that the normal nucleated cells of an affected individual will express one normal copy of the BRCA-1 protein and one truncated copy, whereas their tumor cells are likely to possess two altered copies of the protein.

Antibodies capable of detecting the amino-terminus (N-terminus) of the BRCA-1 protein and antibodies capable of detecting the C-terminus of the BRCA-1 protein are known. These antibodies have been used to localize BRCA-1 protein to particular regions of normal cells and tumor cells (see Ralph Scully el al., *Location of BRCA-1 in Human Breast Cells and Ovarian Cells*, SCIENCE, Vol. 272, Apr. 5, 1996, at 123–124) and, more recently, have been used to monitor expression and localization of protein expressed from transfected constructs containing selected regions of the BRCA-1 protein (see Cindy A. Wilson et al., *Differential Subcellular Localization Expression and Biological Toxicity* . . . , ONCOGENE, Vol. 14, January 1997, at 1–16).

Antibodies capable of detecting the N-terminus and C-terminus regions of the BRCA-2 protein are also available.

Based upon some of the above-referenced discoveries, Myriad Genetics, Inc. of Salt Lake City, Utah, developed a comprehensive BRCA-1 and BRCA-2 DNA sequence analysis which is marketed under the trade designation BRACAnalysis™ comprehensive BRCA-1 and BRCA-2 sequence analysis for susceptibility to breast and ovarian cancer. This genetic analysis reportedly identifies genetic mutations in the entire protein-coding sequences and additional adjacent areas in both the BRCA-1 and BRCA-2 genes. The cost or fee for this genetic analysis is reportedly $2,400.

Due to the complex and comprehensive nature of this DNA-based genetic analysis and the resulting higher cost, it is primarily intended for individuals who are at high risk of hereditary breast or ovarian cancer and those with a diagnosis of breast (especially premenopausal) or ovarian cancer.

Accordingly, there is a need for the development of a less complex and therefore lower cost method for determining cancer susceptibility.

It is therefore the object of the present invention to develop a general screening method for determining susceptibility to breast and ovarian cancer and to other cancers associated with such susceptibility.

It is a more particular object to develop an antibody-based method to detect reduction or loss of the C-terminus regions of BRCA-1 or BRCA-2 protein, which is indicative of a gene mutation.

It is another object of the present invention to develop a test kit for use in conjunction with the developed method.

SUMMARY OF THE INVENTION

The present invention therefore provides an antibody-based method for determining a patient's susceptibility to certain types of cancer(s), which method targets a specific alteration or mutation of a protein expressed in epithelial cells which is deemed responsible for early-onset or development of said cancer(s), wherein a clinically significant percentage of such protein mutations result in the production of a foreshortened protein from which a specific sequence or region is missing.

The present invention more particularly provides an antibody-based method for determining the presence of mutated BRCA-1 or BRCA-2 protein (hereinafter generally referred to as "BRCA protein") in cells expressing this protein, wherein the method comprises:

preparing a first and a second equal quantity of cells that express the BRCA protein;

administering a quantity of a first primary antibody to the first quantity of cells and an equal quantity of a second primary antibody to the second quantity of cells;

measuring antibody reactivity within the first and second quantities of cells; and comparing the measured antibody reactivities to determine the presence of mutated BRCA protein in the first and second quantity of cells;

wherein unmutated BRCA protein contains amino-terminus and carboxy-terminus regions, wherein mutated BRCA protein is typically a foreshortened protein from which carboxy-terminus regions are missing, wherein the first primary antibody used in the inventive method is capable of detecting or reacting with the amino-terminus regions of the BRCA protein, wherein the second primary antibody is capable of detecting or reacting with the carboxy-terminus regions of the BRCA protein, and wherein a difference in the measured antibody reactivities indicates the presence of mutated BRCA protein in the first and second quantity of cells.

The present invention also identifies a non-invasive source of normal cells that express the BRCA protein and provides test kits for use in conjunction with the above-referenced antibody-based method.

The foregoing and other features and advantages of the present invention will become more apparent from the following description.

DESCRIPTION OF THE PREFERRED EMBODIMENT

The present inventive method targets a specific alteration of the BRCA protein—namely, the reduction or loss of the C-terminus regions of these proteins. Due to the high incidence of BRCA gene mutations that result in foreshortened proteins from which these regions are missing, the present method is considered a simple and reliable screening technique that provides a clear positive result. The inventive method could, however, provide an ambiguous negative result.

In particular, a positive result in the method or assay described herein can be considered definitive proof that the tested individual carries a mutated allele. A negative result would indicate that either the individual lies within the 12% of those individuals whose allelic mutations fail to produce protein truncation, or that the individual carries an unmutated allele.

By way of the present invention, a non-invasive source of normal cells that express the BRCA-1 protein (and to a lesser extent the BRCA-2 protein) has been identified. As will be readily apparent to those skilled in the art, the availability of a non-invasive source of normal cells expressing these proteins greatly reduces the cost of the inventive screening technique and renders it capable of use in conjunction with mailer or test kits that serve as a means for the unassisted collection of cell samples from individuals undergoing this screening analysis.

The non-invasive source of normal cells that has been identified constitutes epithelial cells from the inner cheeks (i.e., buccal cells). These cells can be easily scraped with a cotton swab, deposited in a liquid medium by the test subject and mailed to a central location for testing.

As alluded to above, the present inventive method is based upon the hypothesis that cells of an affected individual will express 50% of the BRCA protein having equal numbers of N-terminus and C-terminus regions, and 50% of the BRCA protein having a reduced number of C-terminus regions. This noted imbalance between the N-terminus and C-terminus regions in these proteins is detected by: administering an antibody capable of detecting or reacting with the N-terminus regions to a first cell sample; administering an antibody capable of detecting or reacting with the C-terminus regions to a second equivalent cell sample; measuring antibody reactivities within the cell samples; and comparing the measured antibody reactivities to determine the presence of mutated BRCA protein in the cell samples. Any difference between the measured antibody reactivities would indicate the presence of truncated copies of the protein.

The present invention is suitable for use with cells that express the BRCA protein. These cells may be obtained from any region of the human body that is free of tumor or precancerous tissue including, but not limited to, white blood cells, skin and lymph nodes. These cells may also be obtained from tumor tissue including breast, ovary, colon and prostate tumor tissue. As noted hereinabove, it is preferred that the source of cells used in the present invention constitute a non-invasive source such as epithelial cells, and more preferably, buccal cells.

Preparation of the above-referenced cells, for use in conjunction with the present inventive method, may be performed in accordance with conventional methods and techniques. For example, freshly isolated, monodispersed single cells may be cytospin deposited and then fixed in a 50:50 acetone-methanol solution. Tissue, snap frozen in liquid nitrogen, may be cryostat sectioned, while tissue fixed in buffered formalin ($\leq 4\%$ formaldehyde) may be embedded in paraffin and then microtome sectioned.

In a preferred embodiment, single cells and small clusters of buccal cells are obtained by vigorously rubbing the inner cheek of a test subject with a cotton swab moistened with phosphate buffered saline (PBS). The cotton swab is then submerged in a quantity of PBS contained in a vial and the cells released therefrom through agitation. Cells are then counted (e.g., using a hemocytometer), diluted to 20,000 cells/ml, cytospin deposited, fixed in a 50:50 acetone-methanol solution, and stored at $-20°$ C. Cells may be stored at this temperature, in sealed boxes, for 1 to 4 months.

In a more preferred embodiment of the present inventive method, the imbalance between the N-terminus and C-terminus regions of the BRCA protein is detected by: administering a quantity of an antibody which reacts with the N-terminus regions of the protein (hereinafter referred to as a "primary" antibody) to a first cell sample; adding an equal quantity of another antibody which reacts with the C-terminus regions of the protein (hereinafter also referred to as a "primary" antibody) to a second equivalent cell sample; administering a quantity of a biotin labeled secondary antibody (which serves as a color detection device by reacting with a determinant on the primary antibodies) to the first and second cell samples; adding a quantity of an enzyme complex (that serves to mark the location of antibody reactivity within the test sample) to the respective cell samples; and then staining and counterstaining the cells in each sample prior to determining and comparing primary antibody reactivity.

Primary antibodies capable of detecting the N-terminus regions of the BRCA-1 protein include antibodies prepared by immunization using a peptide sequence representative of BRCA-1 protein amino acids 2–21. In a preferred embodiment, a rabbit polyclonal IgG antibody, sold by Santa-Cruz Biotechnology, Inc., 2161 Delaware Avenue, Santa Cruz, Calif. 95060-5706, under the trade designation "BRCA-1 D-20" (product no. sc641), is employed.

Primary antibodies capable of detecting the C-terrninus regions of the BRCA-1 protein, that are suitable for use in the present invention, include antibodies prepared by immunization using a peptide sequence representative of BRCA-1 protein amino acids 1843–1862. In a preferred embodiment, a rabbit polyclonal IgG antibody, sold by Santa-Cruz Biotechnology under the trade designation "BRCA-1 C-20" (product no. sc-642), is employed.

Primary antibodies capable of detecting the N-terminus regions of the BRCA-2 protein include antibodies prepared by immunization using a peptide sequence representative of BRCA-2 protein amino acids 3–19. In a preferred embodiment, a goat polyclonal IgG antibody, sold by Santa-Cruz Biotechnology, Inc. under the trade designation "BRCA-2I-17" (product no. sc1818), is employed.

Primary antibodies capable of detecting the C-terminus regions of the BRCA-2 protein, that are suitable for use in the present invention, include antibodies prepared by immunization using a peptide sequence representative of BRCA-2 protein amino acids 3404–3418. In a preferred embodiment, a goat polyclonal IgG antibody, sold by Santa-Cruz Biotechnology, Inc. under the trade designation "BRCA-2 C-15" (product no. sc-1816), is employed.

These primary antibodies are preferably diluted with PBS to concentrations ranging from about 0.5 micrograms ($\mu$g)/milliliter (ml) PBS to about 1.0 $\mu$g/ml for BRCA-1 or from about 2.0 to about 5.0 $\mu$g/ml for BRCA-2 and administered to a quantity of 20,000 cells in amounts ranging from about 0.1 to about 2 ml. (i.e., from about 0.05 $\mu$g to about 2.0 $\mu$g BRCA-1 primary antibody or from about 0.2 $\mu$g to about 10.0 $\mu$g BRCA-2 primary antibody).

Secondary antibodies capable of binding to the primary antibodies, that are suitable for use in the present invention, include antiserim obtained from goats immunized with rabbit immunoglobulin for detection of BRCA-1 primary antibodies and antiserum obtained from rabbits immunized with goat immunoglobulin for detection of BRCA-2 primary antibodies. In a preferred embodiment, a biotinylated, affinity-purified anti-immunoglobulin is employed as the secondary antibody. This antibody is available from Vector Laboratories, Inc., Burlingame, Calif. and constitutes a component in a test kit marketed under the trade designation "Vectastain ABC Kit".

These secondary antibodies are preferably diluted with PBS to concentrations ranging from about 5 to about 10 $\mu$g/ml and administered to a quantity of 20,000 cells in amounts ranging from about 0.01 to about 0.5 ml. (i.e., from about 0.05 $\mu$g to about 5.0 $\mu$g secondary antibody).

Enzyme complexes capable of combining and producing a deposit to mark the location of antibody binding, that are suitable for use in the present invention, include avidin DH and biotinylated horseradish peroxidase H. In a preferred embodiment, an avidin-biotin enzyme complex is employed. This complex can be prepared by mixing 10 ml 10 mM phosphate buffered saline (PBS: pH 7.5, 0.9% saline, 0.1% crystalline grade bovine serum albumin) with two drops of avidin reagent and two drops biotin reagent that constitute components in the test kit marketed by Vector Laboratories, Inc. under the trade designation "Vectastain ABC Kit" and is preferably administered to a quantity of 20,000 cells in amounts ranging from about 0.1 to about 0.2 microliters ($\mu$l).

Suitable chromogens and counterstains useful in the present invention constitute precipitate producing chromogens and counterstains that include di-aminobenzidine tetrahydrochloride (DAB) with hematoxylin stain or 3-amino-9-ethylcarbazole (AEC) with eosin stain. It is preferred that DAB be employed to produce the precipitate and that hematoxylin be employed as a counterstain in the practice of the present invention.

The measurement of antibody reactivities within the cell samples, in accordance with the present invention, may be accomplished by way of known conventional methods. For example, measurement or quantification may be carried out by optical microscopic evaluation where the intensity of cellular reactivity is rated on a particular scale (e.g., on a 0–4+ scale) or color intensity may be read mechanically using an image analyzer which scans and quantifies color intensity, providing a comparative numerical value result. Quantification may also be carried out by enzyme linked immunosorbent assay (ELISA), in which cells affixed to 96 well plates serve as the antigen attached to the solid phase and antibodies (as described hereinabove) with a peroxidase conjugate serve as the assay, in the presence of a chromogen (also as described hereinabove). Additionally, quantification may constitute protein quantification carried out by way of radiolabel or chemiluminescence techniques or procedures or may be performed by a computerized image analysis evaluation.

The test kit intended for use in conjunction with the present inventive method preferably contains a quantity of sterile swabs, a vial containing PBS for moistening the swab(s) prior to cell collection, and a second vial containing conventional tissue culture media for storing the collected cells during mailing to a central location for testing.

The present invention is described in more detail with reference to the following Examples which are for purposes of illustration only and are not to be understood as indicating or implying any limitation on the broad invention described herein.

WORKING EXAMPLES

Components Used

KIT 1: a reagent kit containing: blocking serum (goat); biotinylated, affinity-purified
- anti-immunoglobulin (goat anti rabbit) (i.e., concentrated second antibody);
  reagent A (avidin DH); and reagent B (biotinylated horseradish peroxidase H),
- in addition to three mixing bottles (one for the diluted blocking serum or agent, one for the diluted biotinylated second antibody, and one for the diluted avidin-biotin enzyme complex), marketed under the trade designation "Vectastain ABC Kit" (product no. PK4005), by Vector Laboratories, Inc.

KIT 2: a di-aminobenzadine (DAB) substrate reagent kit for peroxidase containing:
- buffer, hydrogen peroxide, DAB, and nickel solution (not used), marketed under the trade designation "DAB Substrate Kit for Peroxidase" (product no. SK4100), by Vector Laboratories, Inc. A DAB solution was prepared by mixing 100ml tap water with 4 drops buffer, 4 drops hydrogen peroxide, and 8 drops DAB.

PRIMARY ANTIBODY N:
- a 1 $\mu$g/ml solution of a rabbit polyclonal IgG antibody (capable of detecting the N-terminus regions of the BRCA-1 protein) in PBS. The antibody is marketed under the trade designation "BRCA-1 D-20" (product no. sc641) by Santa-Cruz Biotechnology, Inc.

PRIMARY ANTIBODY C:
- a 1 $\mu$g/ml solution of a rabbit polyclonal IgG antibody (capable of detecting the C-terminus regions of the BRCA-1 protein) in PBS. The antibody is marketed under the trade designation "BRCA-1 C-20" (product no. sc642) by Santa-Cruz Biotechnology, Inc.

SECONDARY ANTIBODY:
- a 7.5 $\mu$g/ml solution of biotinylated, affinity-purified anti-immunoglobulin obtained from KIT 1 (capable of binding rabbit IgG) in PBS.

PBS: 10 mM phosphate buffered saline comprising 0.9% saline and 0.1% crystalline grade bovine serum albumin and having a pH of 7.5.

AVIDIN-BIOTIN:

an avidin-biotin enzyme complex prepared by mixing 2 drops avidin reagent (reagent A) and 2 drops biotin reagent (reagent B) obtained from KIT 1 with 10 ml PBS and by allowing the complex to form at room temperature for thirty minutes.

Cell Preparation

A. A quantity of buccal cells were collected from the oral cavities of 15 normal male and female adults with cotton swabs moistened with PBS. These adults were in good health with no history of illness and ranged in age from 20 to 52 years. The cotton swabs used to collect the cells were placed in separate glass vials containing a quantity of PBS and the vials agitated to release the cells from the cotton swabs. The released cells from each swab were counted using a BRIGHTLINE™ hemocytometer (manufactured by Fisher Scientific Co., Pittsburgh, Pa.) and diluted with PBS to a concentration of 20,000 cells/ml. The cells were then cytospin deposited using a CYTOSPIN3™ centrifuge sold by Shandon, Inc., Lerner Laboratories, 171 Industry Drive, Pittsburgh, Pa. 15275-1015. The cytospin deposited cells were then used to prepare 50 samples with each sample comprising two microscope slides containing equal quantities of cells from the same test subject. The cells contained on the prepared pairs of slides were then fixed for seven (7) minutes in a 50:50 acetone-methanol solution at −20° C. and then rinsed twice for 15 minutes in PBS using a mechanical rotator for agitation.

The rinsed slides were then transferred to a slide tray having humidified chamber type holders that allowed the slides to lie flat so that reagents could be deposited onto the region of each slide containing the cells. Excess PBS was then removed from each slide using a suction pipette and 200 μl of 7.5 μg/ml goat normal blocking agent (obtained from KIT 1) in PBS was added directly to each slide over the site where the cells were located. The slide tray was then covered with plastic wrap and incubated at room temperature for 30 minutes.

Excess blocking agent was then removed from each slide using a suction pipette.

B. Normal tissue and tumor tissue samples obtained from 35 female adults diagnosed with ovarian cancer were prepared by buffered formalin fixation and paraffin embedment. Once the tissue was embedded in paraffin blocks, the blocks were microtome sectioned to a thickness of 5 microns. Sections from each test subject were then used to prepare 35 samples with each sample comprising two sets of two slides, the first set of which contained slides having equal quantities of normal cells and the second set of which contained slides having equal quantities of tumor cells from the same test subject.

Sample Preparation

A quantity of 200 μl of PRIMARY ANTIBODY N was added to one slide in each sample set over the regions where the cells were located. A quantity of 200 μl of PRIMARY ANTIBODY C was then added to the remaining slide in each set. The slide tray was then covered with plastic wrap and the slides incubated first for 60 minutes at room temperature, and then overnight at 4° C.

The following day, the slides were allowed to come to room temperature for 30 minutes. The slides were then washed twice for five minutes with cold PBS.

Excess PBS was removed from each slide with a vacuum suction and then a quantity of 200 μl of SECONDARY ANTIBODY was added to each slide over the regions where the cells were located. The slide tray was then covered with plastic wrap and the slides incubated for 30 minutes at room temperature.

The slides were then removed from the slide tray, placed in glass racks connected to a mechanical rotor and rinsed for 5 minutes with PBS. The slides were then placed back into the slide tray and the excess PBS was removed with vacuum suction. A quantity of 4 drops of AVIDIN-BIOTIN was then added to each slide over the regions where the cells were located. The slide tray was then covered with plastic wrap and incubated at room temperature for one hour.

The PBS rinsing procedure was then repeated.

Excess PBS was then removed from each slide and a quantity of 4 drops of DAB solution was immediately added over the regions were the cells were located. The slides were then incubated at room temperature for 7 minutes. The DAB solution was then drained from each incubated slide and the slides rinsed under running tap water for 5 minutes.

The slides were then counterstained lightly with hematoxylin and dehydrated by passing the slides through solutions having increasing concentrations of alcohol and zylenes. The slides were then drained and coverslips placed thereon. The slides were then cured for one hour before reading. To preserve color, the slides were protected from direct light.

Test Methods

Antibody Reactivity (0–4+scale)—an optical microscopic evaluation where cells are stained with di-amino benzadine (DAB) solution prepared from KIT 2 and counterstained with hematoxylin and where the intensity of color development, which is directly proportional to the intensity of antibody reactivity, is read at 200× magnification using a 0–4+ scale for grading of color. Colors range from a faint trace of beige (0+/−) to an intense chocolate brown color (3+–4+). Intensities of reactivity of paired slides receiving PRIMARY ANTIBODY N and PRIMARY ANTIBODY C respectively are compared. A difference in the intensities of reactivity is indicative of a mutation on one BRCA-1 allele that has resulted in protein truncation.

Molecular Analysis—a molecular analysis for detecting gene alteration. In this analysis, DNA is prepared from test tissue, tested by polymerase chain reaction (PCR) using primer sets which amplify the 24 exons of the BRCA-1 gene to obtain PCR products. The PCR products are then examined for gene alteration by analysis for single strand conformational polymorphism (SSCP). These procedures constitute conventional procedures described and detailed in the following publication: Donna Shattuck-Eidens et al., *A Collaborative Survey of 80 Mutations . . .* , J. Am. Med. Ass'n, Vol. 273 No. 7, Feb. 15, 1995, at 535–541.

EXAMPLES 1 TO 85

In Examples 1 to 85, the cells contained on the above-described sets of slides were tested for Antibody Reactivity. The results are discussed below.

In Examples 1 to 50, where the buccal cells were obtained from a normal control population, the paired slides in each Example each demonstrated an equal intensity of antibody reactivity.

In Examples 51 to 85, where the cells were obtained from an experimental population, the slides in eighteen of the Examples (with each Example comprising two sets of paired slides containing either cells obtained from normal tissue or cells obtained from tumor tissue from the same test subject) all demonstrated an equal intensity of antibody reactivity. This result suggested the absence of a mutation in either the normal or tumor tissue cells. In twelve of the Working Examples, the slides containing cells from normal tissue demonstrated an equal intensity of antibody reactivity while the slides containing cells from tumor tissue demonstrated a reduced intensity of PRIMARY ANTIBODY C reactivity. Such a result suggests the absence of a mutation in the cells obtained from normal tissue and the presence of a non-inherited mutation in the cells obtained from tumor tissue. In the remaining five Working Examples, the slides containing cells from normal tissue demonstrated a 50% reduction in intensity of PRIMARY ANTIBODY C reactivity while the slides containing cells from tumor tissue demonstrated a 50% or 100% reduction in intensity of PRIMARY ANTIBODY C reactivity. This result suggests the presence of a mutation in cells obtained from both normal and tumor tissue which is indicative of an inherited mutation.

The above-described Examples 1 to 85 collectively demonstrate that the presence of BRCA-1 mutations in cell preparations consequent to an inherited gene mutation resulting in protein truncation and, therefore, susceptibility to breast, ovarian, colon or prostate cancer, can be determined in an expedient and accurate manner using the inventive antibody-based assay.

EXAMPLES 86 to 95

In Examples 86 to 95, 10 sets of paired normal and tumor cell samples, each set constituting one Example in the group of Working Examples numbered 51 to 85, were selected and subjected to the above-described Molecular Analysis test method. The results are tabulated in Table 1 hereinbelow.

TABLE 1

SUMMARY OF EXAMPLES 86 to 95

| Example No. | Antibody Reactivity[1] | | Molecular Analysis[2] | |
|---|---|---|---|---|
| | normal cells | tumor cells | normal cells | tumor cells |
| 86 | − | − | − | − |
| 87 | − | − | − | − |
| 88 | − | − | − | − |
| 89 | − | − | − | − |
| 90 | − | − | + | + |
| 91 | − | + | − | + |
| 92 | − | + | + | + |
| 93 | − | + | + | + |
| 94 | + | + | + | + |
| 95 | + | + | + | + |

[1]"+" = difference in intensities of reactivity noted
"−" = no difference noted
[2]"+" = gene alteration identified
"−" = no gene alteration identified Examples 94 and 95 demonstrate that a positive result in the inventive method or assay as described herein can be considered definitive proof that the tested individual carries a mutated allele. Examples 86 to 95 collectively demonstrate that the results rendered by the present inventive method are confirmed by molecular analysis in 80% of the Examples tested. The discrepancies (e.g., false negative readings) demonstrated by Examples 90, 92 and 93 may be explained by the fact that not all base mutations result in a change of the encoded amino acid, leaving the protein sequence unaltered. Such discrepancies may also be explained by the fact that mutations may not result in a reading frame shift and/or premature termination, which would also leave the protein sequence unaltered.

It should be understood that the invention is not limited to the particular embodiment shown and described herein, but that various changes and modifications may be made without departing from the spirit or scope of the claimed invention.

We claim:

1. An antibody-based method for determining the presence of mutated BRCA protein in cells expressing the protein, wherein unmutated BRCA protein contains amino-terminus and carboxy-terminus regions and wherein mutated BRCA protein is typically a foreshortened protein from which carboxy-terminus regions are missing, wherein the method comprises:

preparing a first and a second equal quantity of cells that express the BRCA protein, wherein the first and the second equal quantity of cells are obtained from one test subject;

administering a quantity of a first primary antibody capable of detecting or reacting with the amino-terminus regions of the BRCA protein to the first quantity of cells;

administering an equal quantity of a second primary antibody capable of detecting or reacting with the carboxy-terminus regions of the BRCA protein to the second quantity of cells;

measuring antibody reactivity within the first and second quantity of cells; and comparing the measured antibody reactivity within the first quantity of cells to the measured antibody reactivity within the second quantity of cells to determine the presence of mutated BRCA protein in the first and second quantity of cells, wherein a difference between the measured antibody reactivity within the first quantity of cells and the measured antibody reactivity within the second quantity of cells indicates the presence of mutated BRCA protein in the first and second quantity of cells.

2. The method of claim 1, wherein the method further comprises:

administering equal quantities of a secondary antibody capable of binding to the primary antibodies to the first and second quantity of cells containing either the first or second primary antibody;

adding equal quantities of an enzyme complex capable of marking locations of antibody binding to the first and second quantity of cells; and then staining and counterstaining the first and second quantity of cells prior to measuring antibody reactivity.

3. The method of claim 1, wherein the cells expressing the BRCA protein are buccal cells.

4. The method of claim 1, wherein the BRCA protein is BRCA-1 protein, and wherein the first primary antibody is an antibody prepared by immunization using a peptide sequence consisting of BRCA-1 protein amino acids at position 2-21.

5. The method of claim 4, wherein the first primary antibody is a rabbit polyclonal IgG antibody.

6. The method of claim 1, wherein the BRCA protein is BRCA-1 protein, and wherein the second primary antibody is an antibody prepared by immunization using a peptide sequence representative of BRCA-1 protein amino acids at position 1843-1862.

7. The method of claim 6, wherein the second primary antibody is a rabbit polyclonal IgG antibody.

8. The method of claim 1, wherein the BRCA protein is BRCA-2 protein, and wherein the first primary antibody is an antibody prepared by immunization using a peptide sequence representative of BRCA-2 protein amino acids at position 3-19.

9. The method of claim 8, wherein the first primary antibody is a goat polyclonal IgG antibody.

10. The method of claim 1, wherein the BRCA protein is BRCA-2 protein, and wherein the second primary antibody is an antibody prepared by immunization using a peptide sequence representative of BRCA-2 protein amino acids at position 3404-3418.

11. The method of claim 10, wherein the second primary antibody is a goat polyclonal IgG antibody.

12. The method of claim 2, wherein the BRCA protein is BRCA-1 protein, and wherein the secondary antibody comprises antiserum obtained from goats immunized with rabbit immunoglobulin.

13. The method of claim 12, wherein the secondary antibody comprises a biotinylated, affinity-purified anti-immunoglobulin.

14. The method of claim 2, wherein the BRCA protein is BRCA-2 protein, and wherein the secondary antibody comprises antiserum obtained from rabbits immunized with goat immunoglobulin.

15. The method of claim 2, wherein the enzyme complex is selected from the group consisting of avidin DH and biotinylated horseradish peroxidase H.

16. The method of claim 15, wherein the enzyme complex comprises an avidin-biotin enzyme complex.

17. The method of claim 2, wherein the first and second quantity of cells are stained with a precipitate producing chromogen selected from the group consisting of di-aminobenzidine tetrahydrochloride and 3-amino-9-ethylcarbazole, and wherein the first and second quantity of cells are counterstained with a stain selected from the group consisting of hematoxylin stain and eosin stain.

18. The method of claim 17, wherein the precipitate producing chromogen is di-aminobenzidine tetrahydrochloride, and wherein the counterstain is hematoxylin stain.

19. The method of claim 1, wherein the antibody reactivity within the first and second quantity of cells is measured using: an optical microscopic evaluation method; an enzyme linked immunosorbent assay; protein quantitation by radiolabel or chemiluminescence; or a computerized image analysis evaluation.

20. The method of claim 1, wherein the cells expressing the BRCA protein are epithelial cells.

21. The method of claim 20, wherein the epithelial cells expressing the BRCA protein are obtained from a non-invasive source of epithelial cells.

22. An antibody-based method for determining the presence of mutated BRCA protein in buccal cells, wherein unmutated BRCA protein contains amino-terminus and carboxy-terminus regions and wherein mutated BRCA protein is typically a foreshortened protein from which carboxy-terminus regions are missing, wherein the method comprises:

preparing a first and a second equal quantity of cells that express the BRCA protein, wherein the first and the second equal quantity of cells are obtained from one test subject;

administering a quantity of a first primary antibody capable of detecting or reacting with the amino-terminus regions of the BRCA protein to the first quantity of cells;

administering an equal quantity of a second primary antibody capable of detecting or reacting with the carboxy-terminus regions of the BRCA protein to the second quantity of cells;

measuring antibody reactivity within the first and second quantity of cells; and comparing the measured antibody reactivity within the first quantity of cells to the measured antibody reactivity within the second quantity of cells to determine the presence of mutated BRCA protein in the first and second quantity of cells, wherein a difference between the measured antibody reactivity within the first quantity of cells and the measured antibody reactivity within the second quantity of cells indicates the presence of mutated BRCA protein in the first and second quantity of cells.

* * * * *